(12) United States Patent
Krauss et al.

(10) Patent No.: US 11,039,780 B2
(45) Date of Patent: Jun. 22, 2021

(54) SYSTEM AND METHOD FOR SEIZURE DETECTION AND RESPONSIVITY TESTING

(71) Applicant: THE JOHNS HOPKINS UNIVERSITY, Baltimore, MD (US)

(72) Inventors: Gregory Krauss, Baltimore, MD (US); Nathan Crone, Silver Spring, MD (US)

(73) Assignee: The Johns Hopkins University, Baltimore, MD (US)

( * ) Notice: Subject to any disclaimer, the term of this patent is extended or adjusted under 35 U.S.C. 154(b) by 422 days.

(21) Appl. No.: 15/284,695

(22) Filed: Oct. 4, 2016

(65) Prior Publication Data
US 2017/0095194 A1 Apr. 6, 2017

Related U.S. Application Data

(60) Provisional application No. 62/237,029, filed on Oct. 5, 2015.

(51) Int. Cl.
| | | |
|---|---|---|
| *A61B 5/16* | (2006.01) | |
| *A61B 5/0205* | (2006.01) | |
| *A61B 5/00* | (2006.01) | |
| *A61B 5/11* | (2006.01) | |
| *G16H 40/67* | (2018.01) | |

(52) U.S. Cl.
CPC .......... *A61B 5/4094* (2013.01); *A61B 5/0022* (2013.01); *A61B 5/0205* (2013.01); *A61B 5/11* (2013.01); *A61B 5/6898* (2013.01); *A61B 5/746* (2013.01); *G16H 40/67* (2018.01)

(58) Field of Classification Search
CPC .......... A61B 5/4094; A61B 5/16; A61B 5/168
See application file for complete search history.

(56) References Cited

U.S. PATENT DOCUMENTS

| | | | |
|---|---|---|---|
| 9,918,670 B2 | 3/2018 | Sabesan | |
| 2002/0099275 A1* | 7/2002 | Schmidt | A61B 5/0002 600/300 |
| 2006/0094970 A1* | 5/2006 | Drew | A61B 5/0006 600/509 |
| 2008/0058664 A1* | 3/2008 | Mirro | A61N 1/37211 600/523 |
| 2009/0062696 A1* | 3/2009 | Nathan | A61B 5/1107 600/595 |
| 2009/0082640 A1* | 3/2009 | Kovach | A61B 5/04001 600/300 |
| 2009/0082641 A1* | 3/2009 | Giftakis | A61N 1/37247 600/300 |

(Continued)

*Primary Examiner* — Niketa I Patel
*Assistant Examiner* — Nathan A Baldwin
(74) *Attorney, Agent, or Firm* — Harrity & Harrity, LLP

(57) ABSTRACT

The present invention is directed to a computer application for seizure detection using biometric data and responsivity testing. The computer application collects biometric data and responsiveness test results from biometric sensors and an interactive user interface in order to identify and confirm seizures and monitor for severity, duration, and permit logging and notification. The computer application collects data such as heart rate, movement, and responsivity testing results. The computer application facilitates caregiver notification of seizures at or before seizure onset if the user has a warning aura and/or during prolonged or severe seizures (e.g. long duration or convulsive movements).

21 Claims, 18 Drawing Sheets

(56) References Cited

U.S. PATENT DOCUMENTS

| | | | |
|---|---|---|---|
| 2009/0083070 A1* | 3/2009 | Giftakis | A61N 1/36135 705/2 |
| 2011/0201944 A1* | 8/2011 | Higgins | A61B 5/4094 600/483 |
| 2011/0251468 A1* | 10/2011 | Osorio | A61B 5/0476 600/300 |
| 2012/0083700 A1* | 4/2012 | Osorio | A61B 5/0472 600/483 |
| 2013/0060167 A1* | 3/2013 | Dracup | A61B 5/11 600/595 |
| 2014/0081090 A1* | 3/2014 | Picard | G06F 19/3418 600/301 |
| 2014/0081347 A1* | 3/2014 | Nelson | A61N 1/36082 607/45 |
| 2015/0157252 A1* | 6/2015 | Sabesan | A61B 5/4094 600/301 |
| 2015/0366518 A1* | 12/2015 | Sampson | A61B 5/7264 600/301 |
| 2016/0100788 A1* | 4/2016 | Sano | A61B 5/121 600/595 |
| 2018/0085000 A1* | 3/2018 | Weffers-Albu | A61B 5/7246 |

* cited by examiner

EDITING SEIZURE EVENT

- Editable fields become active
- Will not overwrite date, but will append existing record

FIG. 4B

EDITING SEIZURE EVENT (W/ TRIGGERS)

- If user indicates possible triggers, a trigger checklist will appear

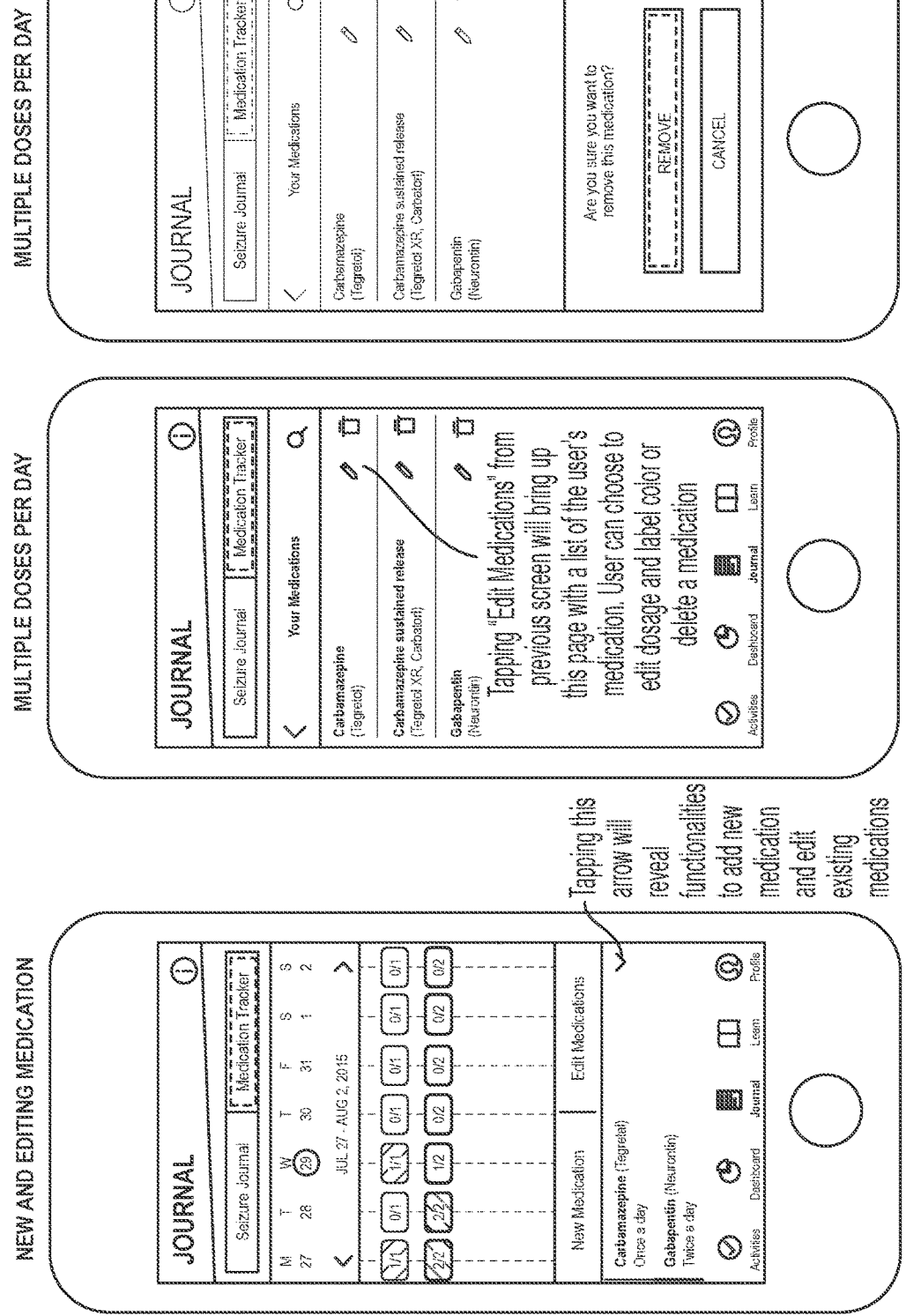

SYSTEM AND METHOD FOR SEIZURE DETECTION AND RESPONSIVITY TESTING

CROSS REFERENCE TO RELATED APPLICATION

This application claims the benefit of U.S. Provisional Patent Application No. 62/237,029 filed on Oct. 5, 2015, which is incorporated by reference, herein, in its entirety.

FIELD OF THE INVENTION

The present invention relates generally to a medical computer application. More particularly, the present invention relates to a system and method for seizure detection and responsivity testing.

BACKGROUND OF THE INVENTION

Seizures can result from a number of causes. Epilepsy is a group of neurological diseases characterized by epileptic seizures. Epileptic seizures are defined as episodes of neurological impairment that vary from brief and nearly undetectable to long periods of vigorous shaking and unresponsiveness. In epilepsy, seizures tend to recur, and have no immediate underlying cause. This can make these seizures difficult to track and predict, leaving patients potentially vulnerable during an episode.

The cause of most cases of epilepsy is unknown, although some people develop epilepsy as the result of brain injury, stroke, brain tumor, or congenital brain malformations. Genetic mutations are linked to a small proportion of the disease. Epileptic seizures are the result of excessive and abnormal cortical nerve cell activity in the brain. A key component in the diagnosis of most types of epileptic seizure is the occurrence of a brief lapse of normal behavioral responses to environmental stimuli. However, seizures rarely occur in the presence of medical personnel that can objectively assess this. As a result, the diagnosis typically relies on first or second hand reports of seizure events by untrained medical personnel. As a result, the diagnosis is often made provisionally and involves ruling out other conditions that might cause similar symptoms. Epilepsy can often be confirmed with an electroencephalogram (EEG) but a normal test does not rule out the condition in all cases. For these reasons, it would be useful to have an app on a device worn by patients that would test their responsiveness during episodes that are provisionally diagnosed as epileptic seizures.

Seizures are unpredictable and can occur when patients do not have immediate access to care. Because of their unpredictable and potentially dangerous nature, it would be advantageous to provide a computer application that can detect and monitor seizures and allow for a caregiver to be contacted.

SUMMARY OF THE INVENTION

The foregoing needs are met by the present invention directed to a method of tracking seizures and responsiveness in a user that includes gathering real-time data from a smart wearable positioned on a body of the user. The smart wearable includes sensors to gather heart rate, an accelerometer, and a gyroscope. The method includes gathering personal data from the user including sleeping and eating habits and gathering real-time responses to surveys and tests when the user is experiencing seizure symptoms. The method includes transmitting the real-time data, the personal data, and the real-time responses to a computing device for processing information regarding the user's seizure. The method also includes transmitting an alert that the user is experiencing a seizure to a contact selected by the user.

In accordance with an aspect of the present invention, the method includes transmitting the alert to the contact after ten minutes of the user experiencing the seizure. The method includes repeating gathering real-time responses to prompts on the wearable until the user stops experiencing the seizure. The method includes gathering trigger data from the user. Additionally, the method includes providing a journal feature to the user for recording information related to the seizure including triggers and medication adherence. The method also includes using a non-transitory computer readable medium programmed for executing the method.

In accordance with an aspect of the present invention, a system for tracking seizures includes a device configured to record user movement and heart rate for a predetermined period. The system also includes a non-transitory computer readable medium (ntcrm) programmed for prompting the user to confirm the user wants to track a seizure. The ntcrm is programmed for presenting the user with a memory game to test responsiveness and recording responsiveness of the user. The ntcrm is also programmed for prompting the user to complete a post-seizure survey and recording the user's post seizure responses. Additionally, the ntcrm is programmed for transmitting an alert that the user is having a seizure to a predetermined contact and transmitting user movement, heart rate, responsiveness and survey responses to a care provider.

In accordance with another aspect of the present invention, the system includes transmitting the alert to the contact depending on the duration and severity of the user's seizure, determined by the user's responses to tests and surveys and by the application's analysis of biometric data. The system includes repeating gathering real-time responses to surveys and tests until the user stops experiencing the seizure and gathering trigger data from the user and relating this to seizure occurrence for subsequent modification of lifestyle, medication adherence, and other habits. The system includes providing a journal feature to the user for recording information related to the seizure including triggers and medications and transmitting an alert if the user has been experiencing a seizure for a time period greater than a predetermined period of time. Additionally, the system includes transmitting an alert to a predetermined care giver if the user is non-responsive to prompts.

In accordance with still another aspect of the present invention, a non-transitory computer readable medium (ntcrm) includes prompting the user to confirm the user wants to track a seizure. The ntcrm includes presenting the user with a memory game to test responsiveness and recording responsiveness of the user. The ntcrm is programmed for prompting the user to complete a post-seizure survey and recording the user's post seizure responses. The ntcrm is also programmed for transmitting an alert that the user is having a seizure to a predetermined contact and transmitting user movement, heart rate, responsiveness and survey responses to a care provider.

In accordance with yet another aspect of the present invention, the ntcrm is programmed for transmitting the alert to the contact depending on the duration and severity of the user's seizure, determined by the user's responses to tests and surveys and by the application's analysis of biometric data. The ntcrm is programmed for repeating gathering real-time responses to surveys and tests until the user stops experiencing the seizure. The ntcrm is programmed for recording trigger data from the user and relating this to seizure occurrence for subsequent modification of lifestyle, medication adherence, and other habits. An alert is transmitted if the user has been experiencing a seizure for a time period greater than a predetermined period of time. An alert is also transmitted to a predetermined care giver if the user is non-responsive to prompts.

BRIEF DESCRIPTION OF THE DRAWINGS

The accompanying drawings provide visual representations, which will be used to more fully describe the representative embodiments disclosed herein and can be used by those skilled in the art to better understand them and their inherent advantages. In these drawings, like reference numerals identify corresponding elements and:

FIG. 2A illustrates an exemplary screen shot of a single day view for a journal feature according to an embodiment of the computer application of the present invention.

FIG. 2B illustrates an exemplary screen shot of a single day view with information for seizure triggers for a journal feature according to an embodiment of the computer application of the present invention.

FIG. 4A illustrates an exemplary screen shot of editing a seizure event for a journal feature according to an embodiment of the computer application of the present invention.

FIG. 4B illustrates an exemplary screen shot of editing seizure events with triggers for a journal feature according to an embodiment of the computer application of the present invention.

FIG. 11A an exemplary screen shot of medication tracking functionality for a journal feature according to an embodiment of the computer application of the present invention.

FIG. 11B illustrates an exemplary screen shot of editing a medication for a journal feature according to an embodiment of the computer application of the present invention.

FIG. 11C illustrates an exemplary screen shot of deleting a medication for a journal feature according to an embodiment of the computer application of the present invention.

DETAILED DESCRIPTION

Figure 1:
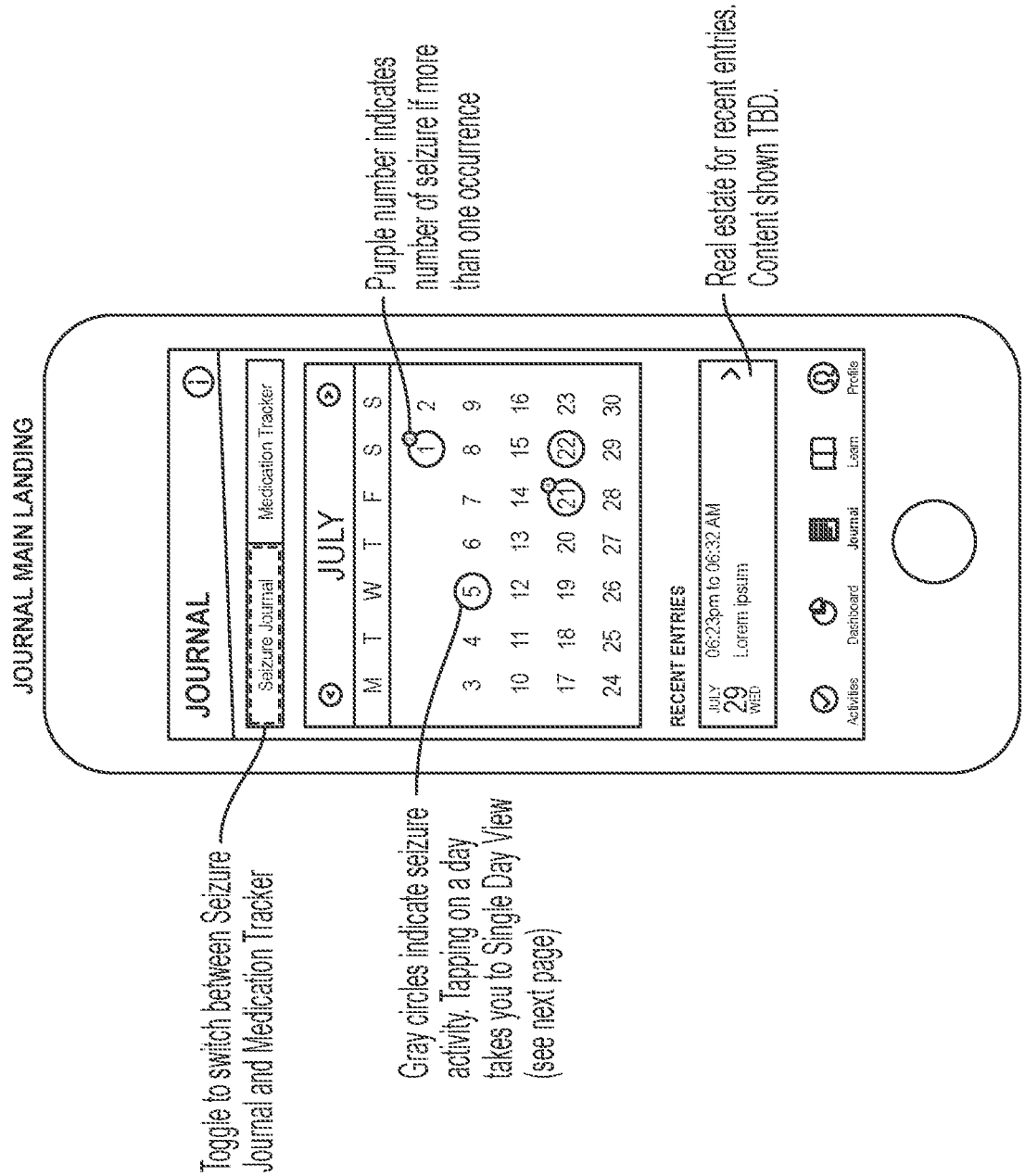
FIG. 1 illustrates an exemplary screen shot of a main landing page for a journal feature according to an embodiment of the computer application of the present invention.

The presently disclosed subject matter now will be described more fully hereinafter with reference to the accompanying Drawings, in which some, but not all embodiments of the inventions are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains, having the benefit of the teachings presented in the foregoing descriptions and the associated Drawings. Therefore, it is to be understood that the presently disclosed subject matter is not to be limited to the specific embodiments disclosed and that modifications and other embodiments are intended to be included within the scope of the appended claims.

The present invention is directed to a computer application for seizure detection using biometric data and responsivity testing. The computer application collects biometric data and responsiveness test results from biometric sensors and an interactive user interface in order to identify and confirm seizures and monitor for severity, duration, and permit logging and notification. The computer application collects data such as heart rate, movement, and responsivity testing results. The computer application facilitates caregiver notification of seizures at or before seizure onset if the user has a warning aura and/or during prolonged or severe seizures (e.g. long duration or convulsive movements).

The computer application is reliant on data collected from sensors in a device such as a smart watch or other suitable smart wearable known to or conceivable by one of skill in the art. The smart watch or smart wearable can include sensors including but not limited to, at least a pulse sensor, an accelerometer, a gyroscope, and a user interface for providing user input and receiving feedback from the user. The pulse sensor can take the form of a photo plethysmography sensor. The photo plethysmography sensor can take the form of laser emitting diode (LED) and a photodiode. The LEDs can emit colored light, such as green colored light, or infrared light. In addition, the device can include wearable wireless EEG sensors/amplifiers as another source of biometric data for seizure detection. The accelerometer and gyroscope can take the form of any suitable accelerometer or gyroscope known to or conceivable by one of skill in the art. The smart watch or wearable can also incorporate a global positioning system (GPS) tracker or can be configured to communicate with the GPS tracker in the user's smartphone, phablet, tablet, or other GPS enabled device. The user interface can be a touchscreen or can include buttons or other means for the user to respond to prompts that test the user's responsivity. The smart watch or smart wearable can also include Bluetooth, wi-fi, cellular network enabling technology or other suitable means for communicating information to the user's smartphone, a caregiver's smartphone, or other hub for information regarding the user's health.

The computer application uses the sensors in the device such as the smart watch or smart wearable to collect data on heart rate, which is increased in a majority of seizures. The accelerometer and gyroscopes collect movement data, in order to identify seizure-type movements and falls. The user interface collects responsivity data from the user, with prompts and questions regarding the user's seizure episode. The data collected can be used for the purposes of identifying seizures, determining the severity of seizures, alerting caregivers, gathering information regarding the user's personal seizure history, and research purposes.

In one embodiment, the computer application in conjunction with the smart watch or wearable allows the user to trigger the continuous collection of movement and heart rate data for up to 10 minutes whenever the user has a seizure. The computer application tests the user's ability to respond to vibration or other prompts on the smart watch or wearable after report of a seizure. The computer application also gives the user the option to send a text message to someone (like a caregiver) reporting the onset of a seizure when you activate the app. The user is prompted by the application to answer a few questions every day to see if the user has had any seizures or missed taking medication. The computer application also allows the user to keep and review a log of seizures and medications, to view a summary of information gathered, and to access educational resources about seizures and their management. Baseline information about health, wellness, and potential seizure triggers can also be collected.

The computer application can prompt the user to complete a number of surveys, tests, and questionnaires that will be described in further detail herein. Surveys can include initial health surveys, post-seizure surveys, daily surveys, and surveys directed to other subject matter. The surveys can include questions regarding seizures, other medical conditions or health information that may impact the occurrence or treatment of seizures. Notifications to respond to surveys can be sent via the smart watch or wearable or via smartphone, or other computing device. The responses can be transmitted back to a health care professional via a server and a suitable network connection. The information collected in these surveys can be used to further tailor the computer application for use in tracking seizures for the specific user and for all users. For instance, a trigger factor for the user could be determined using the information collected by the application. During the seizure, the user's health metrics and movements are also passively tracked by the sensors in the smart watch or wearable. The metrics are reported to the health care provider via a network connection and also possible saved for research purposes. The metrics are recorded for a 10 minute period and the user is prompted for responses during that 10 minute period. Seizure symptoms that exceed the 10 minute period can be indicative of a serious problem. If the seizure symptoms continue on longer than the 10 minute period, the user can have a designated emergency contact or emergency care provider to be contacted to provide the user with immediate assistance.

The computer application is also configured to collect baseline data from the user. For instance, when the user starts using the computer application the user may be prompted to play a brief memory game to compare the results to those collected during a seizure. The user's heart rate at rest is collected for a period of approximately 5 minutes, and the user's heart rate during a stress condition, such as exercise, may also be collected.

When a user is wearing the smart watch or wearable equipped with the computer application of the present invention, the user can either actively engage the computer application to track the seizure at onset of warning signs such as aura, or the seizure symptoms can trigger activation of the tracking function of the application. After the application has been triggered, the user is asked to respond to prompts and play a brief memory game, while experiencing the seizure. The user is also asked to complete a survey after the seizure is completed.

The data gathered from the user's interactions with the computer application during and after seizure, such as survey, sensor data, and behavioral responses, is recorded and transmitted to the caregiver, a physician, and/or a server for further processing and research. The data is combined with other similar data from other users. The personal nature of the data is protected by anonymous codes or other anonymizers applied for tracking the data.

The computer application can also be configured to access health and personal information provided to other applications on the smart watch or wearable or paired smartphone or computing device. Permission for access to this information can be requested by the computer application before the information is accessed. This data includes but is not limited to body measurements (body mass index, body fat percentage, height, body mass, lean body mass, and weight), fitness identifiers (step count, distance walking/running, distance cycling, basal energy burned, active energy burned, flights climbed, Nike Fuel data, other wearable data), vital signs identifiers (heart rate, body temperature, blood pressure systolic, blood pressure diastolic, respiratory rate, results identifiers, oxygen saturation, peripheral perfusion index, blood glucose, number of times fallen, electrodemal activity, inhaler usage, blood alcohol content, forced vital capacity, forced expiratory volume, peak expiratory flow rate, nutrition identifiers, dietary biotin, dietary caffeine, dietary calcium, dietary calcium, dietary carbohydrates, dietary chloride, dietary chromium, dietary copper, dietary energy consumed, dietary fat monounsaturated, dietary fat polyunsaturated, dietary saturated fat, dietary fiber, dietary folate, dietary iodine, dietary iron, dietary magnesium, dietary manganese, dietary molybdenum, dietary niacin, dietary pantothenic acid, dietary phosphorus, dietary potassium, dietary protein, dietary riboflavin, dietary selenium, dietary sodium, dietary sugar, dietary thiamin, dietary vitamin A, dietary vitamin B12, dietary vitamin B6, dietary vitamin C, dietary vitamin D, dietary vitamin E, dietary vitamin K, dietary zinc, dietary water, and UV exposure), category type identifiers (sleep analysis, sedentary state, cervical mucus quality, ovulation test result, menstrual flow, vaginal spotting, and sexual activity), characteristics identifiers (biological sex, blood type, date of birth, Fitzpatrick skin type, and skin tone on a range from I to VI. A way to classify the typical response of different types of skin to ultraviolet (UV) light.), correlation identifiers (blood pressure, food, workout identifier), and additional information such as bedtime and wakeup time.

In use, the computer application is opened on the smart watch or wearable to start recordings of movements and heart rate for the next 10 minutes. A family member or other caregiver may do this part of the task for the user, if the user is unable. The user responds to prompts on the smart watch or wearable to confirm that the user wants to log a seizure and to send a notification about it. The user plays a brief memory game to test responsiveness. If the user cannot complete the game, it will be repeated until the user is able to complete the game. Five minutes after the user completes the game, the user will be asked to complete the brief post-seizure survey (see above). If the user was unable to play the game at all, the user will be asked to complete the survey after 30 minutes. The duration of these seizure tracking tasks will depend on the duration of the seizure and how long it takes for the user to recover. The user may not be able to respond to any of the prompts for responsiveness testing or the post-seizure survey. If this happens or the user is unable to open the app at the start of the seizure, the user may log the seizure after it is over in the seizure diary functionality of the computer application.

In some instances, the present invention includes responsiveness testing during seizure tracking, where patients are asked to do brief cognitive tasks to determine whether they have altered awareness as part of a seizures; the testing occurs intermittently during the seizures and allows determination of the degree and duration of altered awareness. This function is important to identifying seizures and their duration and has applications such as determining driving safety for the patient.

The computer application can ask the user what types of seizures the user has had in the past. Descriptions of the seizures can also be made available to the user via the application. Seizure types include Generalized tonic-clonic (grand mal) (TC), Complex partial (focal dyscognitive) with or without aura (CPS), Simple partial (focal) (SPS), Aura, Absence (petit mal) (ABS), Atonic (drop attack) (ATO), Tonic (TON), Myoclonic (MYO). In conjunction with the information about the types of seizures experienced, the user is also prompted to provide information about the frequency and duration of the seizures by type. Ranges can be provided in order to make the questions easier for the user to answer. The user is asked to provide medication inventory, formulation, dosing information, and side effects experienced as a result of medication. The user can be asked for information related to causes of the user's particular seizures.

An exemplary survey follows:

Time to log your seizure and medication

Button: Dismiss

1. Did you experience any seizures in last 24 hours?
    Button: Yes [move to question 2]
    Button: No [move to question 7]
    Cancel [if selected, copy reads: Please fill out the survey in the activities tab of the Epi-Track iPhone app.
    Button: Dismiss]

2. How many seizures did you have?
    1-?
    Button: Continue [move to question 3]
3. Select seizure type of the first seizure.
    SPS
    CPS
    TC
    TON
    ATO
    ABS
    MYO
    Button: Continue [move to question 4]
4. Did you have a warning of this seizure?
    Button: Yes [move to question 5]
    Button: No [move to question 5]
5. Were you dazed or confused at the time of the seizure?
    Button: Yes [move to question 6]
    Button: No [move to question 6]
6. What possibly triggered the first seizure event? [tap all that apply]
    Missed pill(s)
    Stress
    Lack of sleep
    Fever, infection
    Overexertion
    Head trauma
    Menstrual cycle
    Diet
    Button: Continue [move to question 7]
Interstitial Screen if medications have not been set up:
To start tracking medications, please visit the app on your iPhone to set up medication.
Button: Dismiss
7. Did you take all your medication(s) in the last 24 hours? [Yes, No]
    Button: Yes [move to final screen]
    Button: No [move to question 8]
8. Which medication(s) did you miss? [tap all that apply]
    [List of user's specified medications]
    An exemplary baseline test follows:
Practice Mode
I am the . . . .
Button: Patient
Button: Caregiver
Practice Mode
Get ready to respond.
Tap on button when prompted.
Test 1:
Practice Mode
TAP
Practice Mode
Get ready to respond.
Repeat the tap pattern.

Test 2:
Practice Mode
[Squares]
[If either test is incorrect]
Practice Mode
Next test begins in . . . .
[Countdown]
[If both tests are correct, and baseline is complete]
Practice Completed
Button: Retry
Button: Finish
[If both tests are correct, and baseline is NOT complete]
Practice Completed
Button: Retry
Button: Start Baseline Test
   An exemplary post seizure survey follows:
1. Select seizure type of this seizure.
   SPS
   CPS
   TC
   TON
   ATO
   ABS
   MYO
   Button: Continue
2. Did you have a warning of this seizure?
   Button: Yes
   Button: No
3. Were you aware at the time of the first seizure?
   Button: Yes
   Button: No
4. Was there a trigger that set off this seizure?
   Button: Yes [move to question 5]
   Button: No [push to final screen]
5. What possibly triggered the first seizure event? [tap all that apply]
   Missed pill(s)
   Stress
   Lack of sleep
   Fever, infection
   Overexertion
   Head trauma
   Menstrual cycle
   Diet
   Button: Continue [move to question 7]

The computer application also includes a feature for the user to record data in a journal. The journal allows the user to view all information regarding recorded seizures. The calendar allows for the user to view days when a seizure occurred and also deep dive into a specific seizure occurrence.

An exemplary tracking and response text experience follows:
   Seizure tracking: Start tracking your episode.
      Button: Start
      Tap on the crown of your watch to cancel
      I am the . . . .
      Button: Patient
      Button: Caregiver
   Response Testing:
      Start seizure response test?
      Button: Start
      Tap on the crown of your watch to cancel
      I am the . . . .
      Button: Patient
      Button: Caregiver
      Get ready to respond.
      Tap on button when prompted.
   Test 1:
   TAP
   Get ready to respond.
   Repeat the tap pattern.
   Test 2:
   [Squares]
   [If either test is incorrect]
   Next test begins in . . . .
   [Countdown]
   Completion:
   [If both tests are correct]
   Congrats!
   Sending Data
   Congrats!
   Event Recording Completed
   Congrats!
   Completed in [TIME]
   Button: Log Seizure
   Button: Log in 5 Min.
   Button: Log on iPhone
   Button: Dismiss
   [if log on iPhone is selected]
   Please open the Epi-Track app on your iPhone and complete the post-seizure survey.
   [if Dismiss is selected]
   You can log this seizure event at a later time in the iPhone app.
   Button: Dismiss FIG. 1 illustrates an exemplary screen shot of a main landing page for a journal feature according to an embodiment of the computer application of the present invention. FIG. 1 shows a toggle to switch between the seizure journal and the medication tracker. Circles around a date on the calendar indicate that activity occurred on that date. Tapping on the date takes the user to a single day view (further illustrated in FIG. 2A). Numbers alongside the date indicate the number of seizures that occurred on that date, if more than one. The screen also shows recent activity.

Figures 2A, 2B:
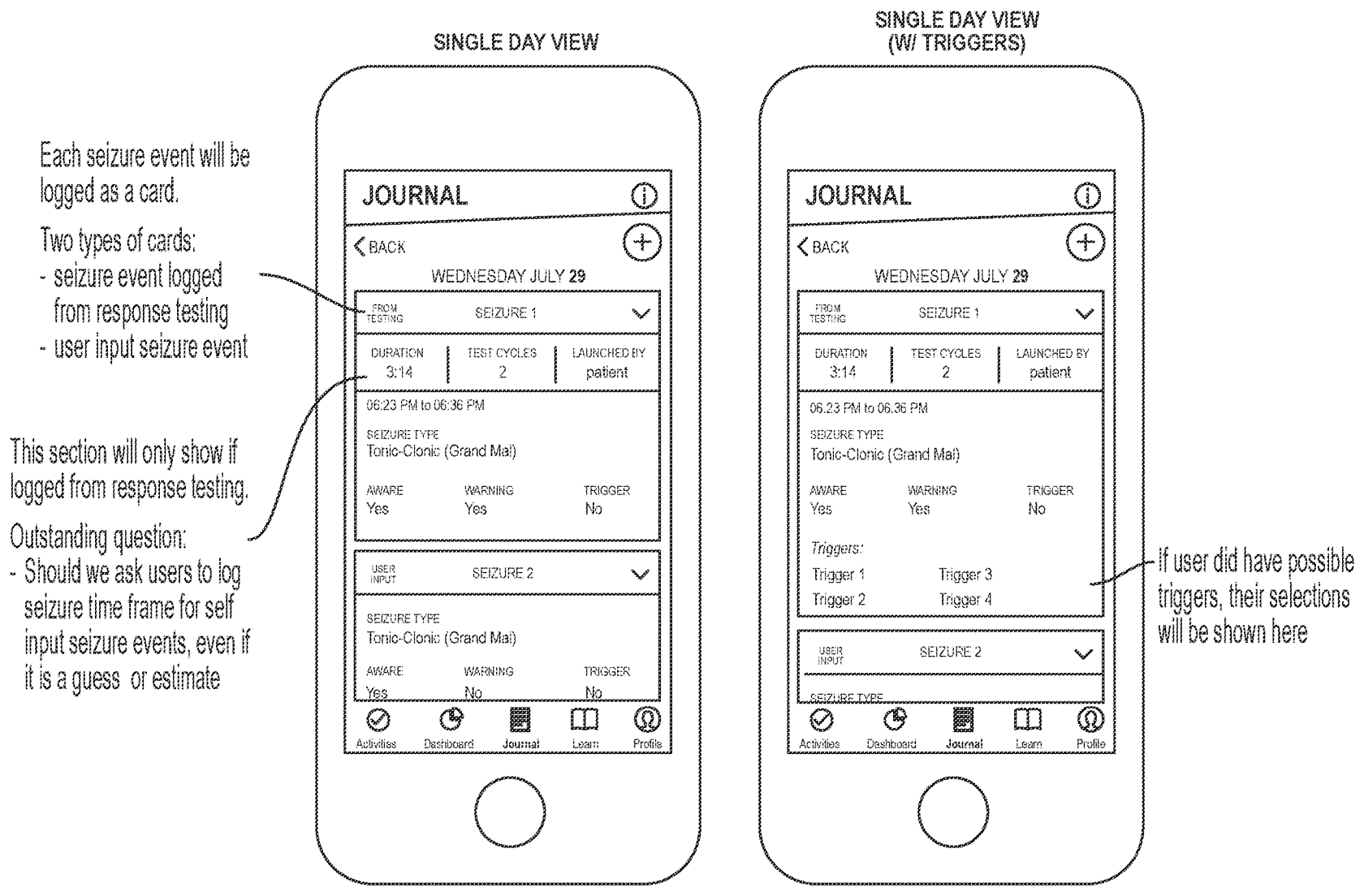

FIG. 2A illustrates an exemplary screen shot of a single day view for a journal feature according to an embodiment of the computer application of the present invention. FIG. 2A shows a single day view that is selected from the calendar. The single day view is shown as a card. The card indicates whether it was a seizure recorded from response testing during the seizure event or later logged by the user or caregiver. If the card was recorded from response testing during the seizure it will list the duration of the seizure, the number of test cycles executed by the user and whether the computer application was launched by the user or the caregiver. The card also includes information about the type of seizure, as illustrated in FIG. 2A. FIG. 2B illustrates an exemplary screen shot of a single day view with information for seizure triggers for a journal feature according to an embodiment of the computer application of the present invention. FIG. 2B adds to the information of FIG. 2A and includes the information related to possible triggers for the seizure event.

Figure 3A:
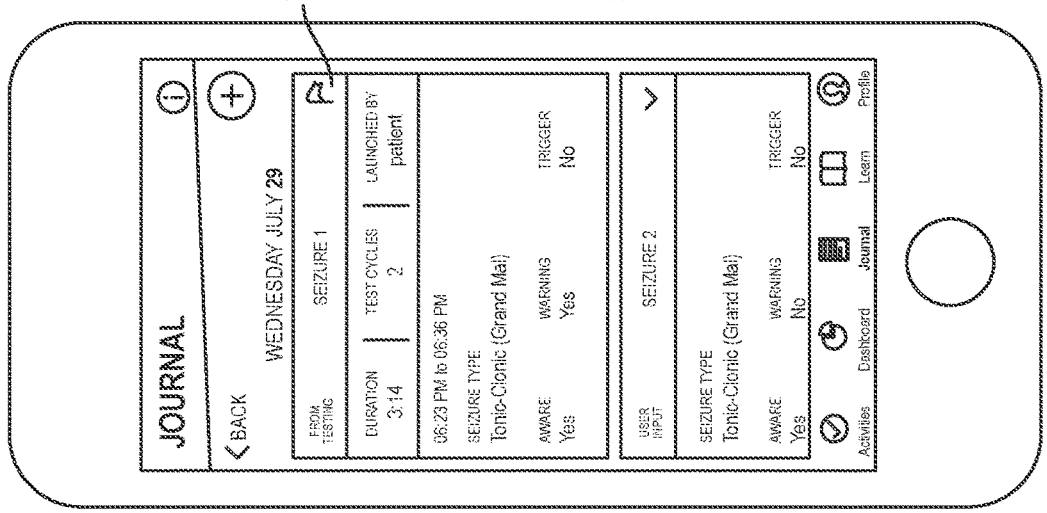
FIG. 3A illustrates an exemplary screen shot of seizure event options for a journal feature according to an embodiment of the computer application of the present invention.
Figure 3B:
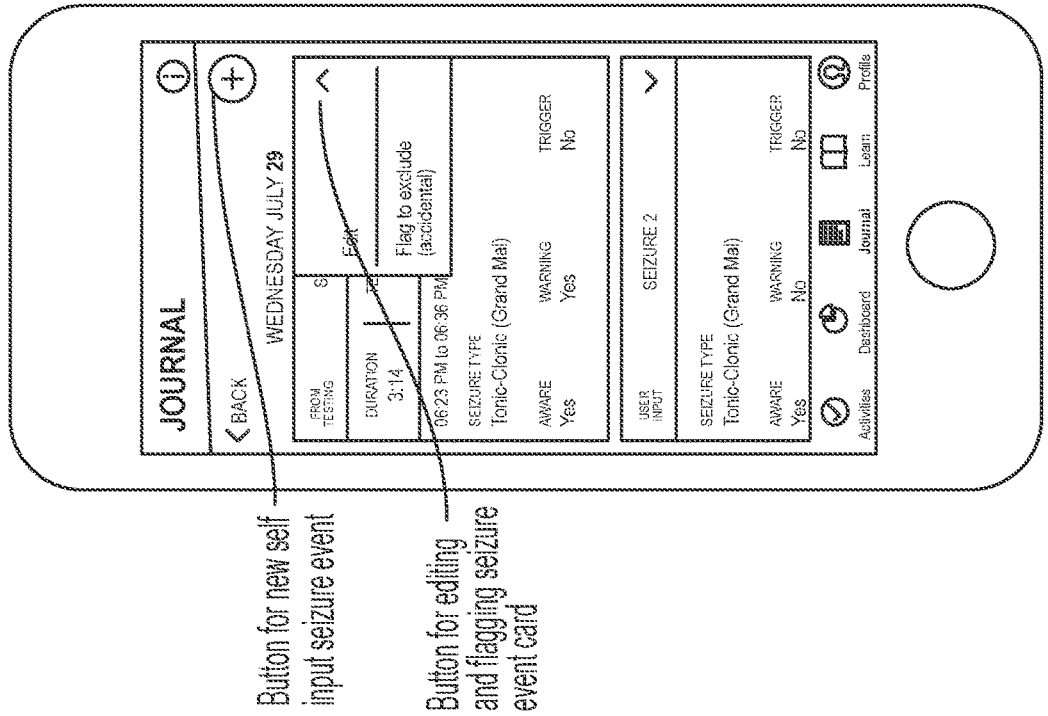
FIG. 3B illustrates an exemplary screen shot of a flagged seizure event for a journal feature according to an embodiment of the computer application of the present invention.

FIG. 3A illustrates an exemplary screen shot of seizure event options for a journal feature according to an embodiment of the computer application of the present invention. FIG. 3A illustrates the button for new self-input seizure events and the buttons for editing and flagging seizure event cards. FIG. 3B illustrates an exemplary screen shot of a flagged seizure event for a journal feature according to an embodiment of the computer application of the present invention. As illustrated in FIG. 3B, the flagged event has a flag indication on the card screen. The flag can be toggled on an off by the user, as necessary.

FIG. 4A illustrates an exemplary screen shot of editing a seizure event for a journal feature according to an embodiment of the computer application of the present invention. FIG. 4B illustrates an exemplary screen shot of editing seizure events with triggers for a journal feature according to an embodiment of the computer application of the present invention. FIGS. 4A and 4B illustrate editing a seizure event and editing a seizure event with triggers. Once the editing mode has be entered the editable fields become active. If the user indicates possible triggers, a trigger checklist will appear, as in FIG. 4B.

Figure 5:
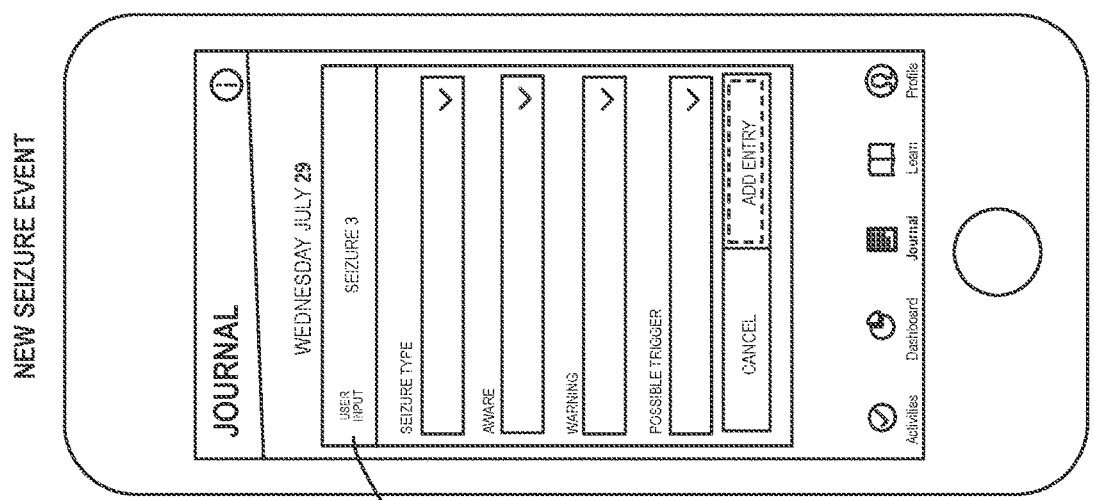
FIG. 5 illustrates an exemplary screen shot of creating a new seizure event for a journal feature according to an embodiment of the computer application of the present invention.

FIG. 5 illustrates an exemplary screen shot of creating a new seizure event for a journal feature according to an embodiment of the computer application of the present invention. As illustrated in FIG. 5 the manual seizure entries are marked as user input. The user can add information about the seizure using the menus on the page.

Figure 6:
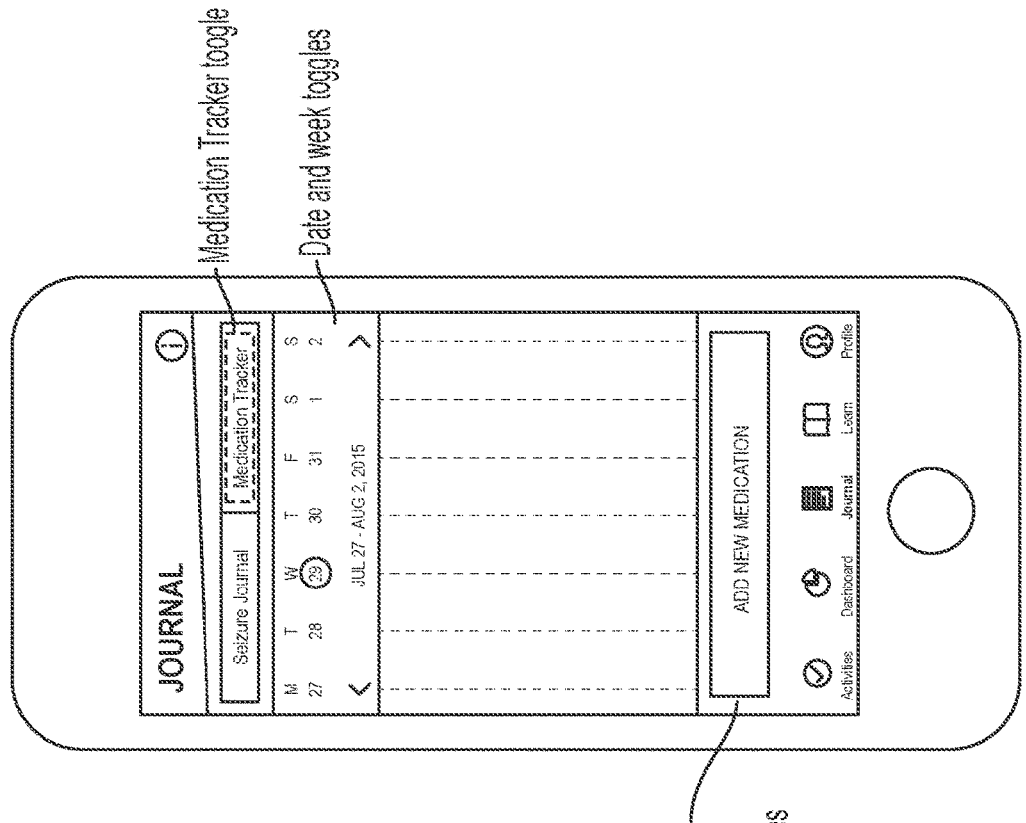
FIG. 6 illustrates an exemplary screen shot of a medication tracker main menu for a journal feature according to an embodiment of the computer application of the present invention.

FIG. 6 illustrates an exemplary screen shot of a medication tracker main menu for a journal feature according to an embodiment of the computer application of the present invention. The medication tracker includes a feature for the user to select in order to add a new medication to the calendar. The user is prompted to add new medications, if they have not already done so through the activities tab or through the daily reminder watch.

Figures 7A, 7B:
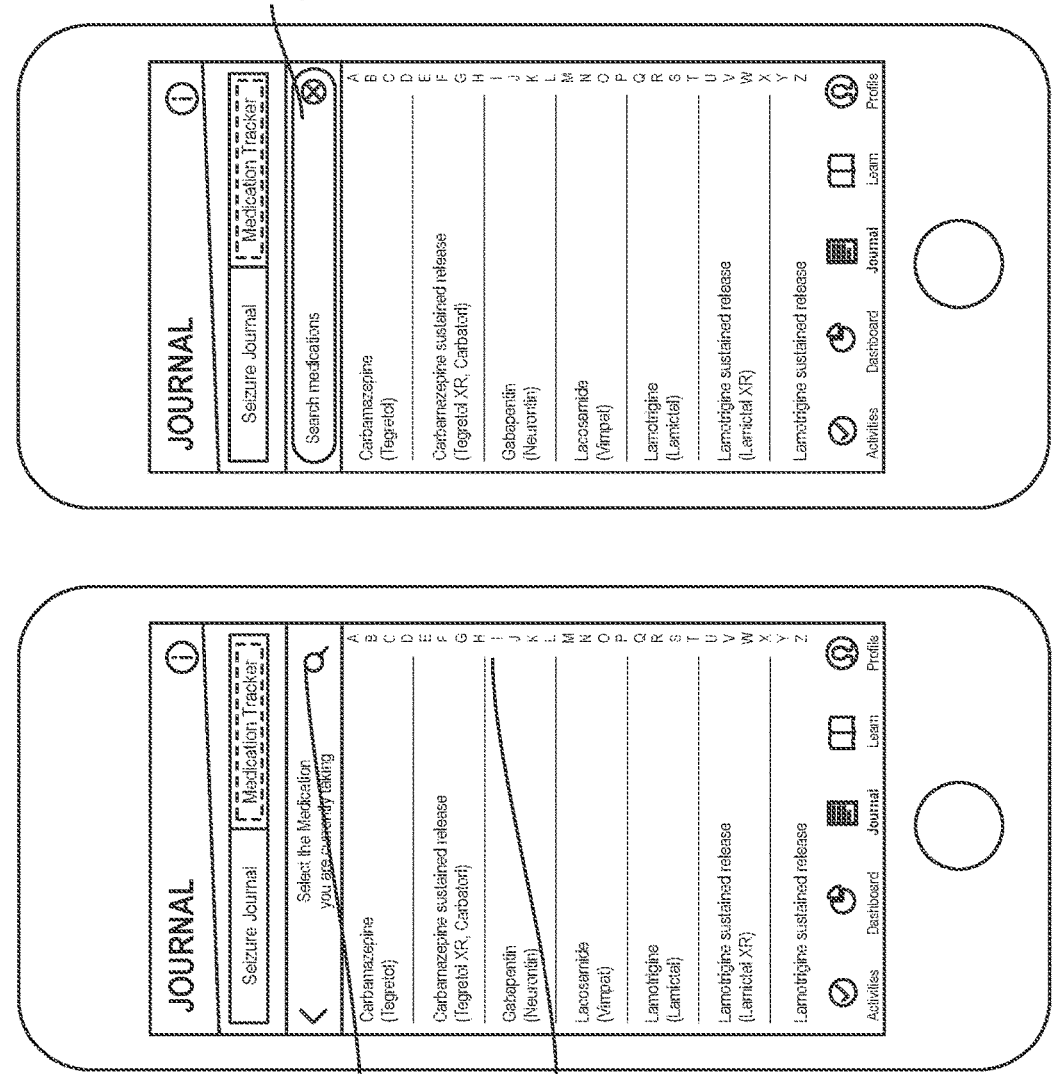
FIG. 7A illustrates an exemplary screen shot of adding a medication for a journal feature according to an embodiment of the computer application of the present invention.
FIG. 7B illustrates an exemplary screen shot of a medication search for a journal feature according to an embodiment of the computer application of the present invention.

FIG. 7A illustrates an exemplary screen shot of adding a medication for a journal feature according to an embodiment of the computer application of the present invention. FIG. 7B illustrates an exemplary screen shot of a medication search for a journal feature according to an embodiment of the computer application of the present invention. Medications can be searched in a list view, selected from the alphabetical list and added to the medication tracker.

Figure 8B:
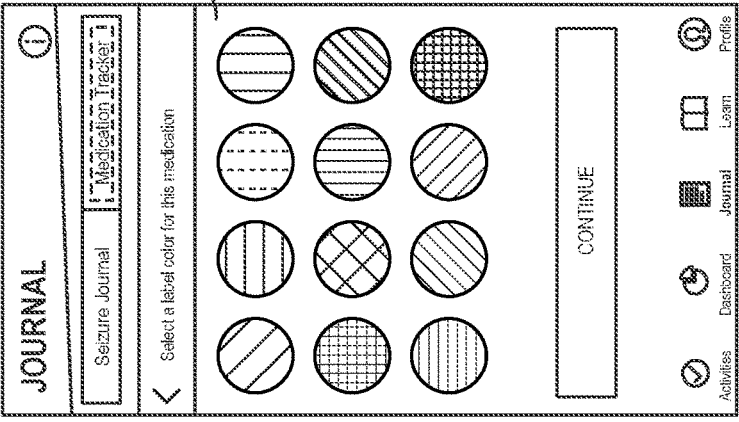
FIG. 8B illustrates an exemplary screen shot of a label color selection for the new medication for a journal feature according to an embodiment of the computer application of the present invention.
Figure 8A:
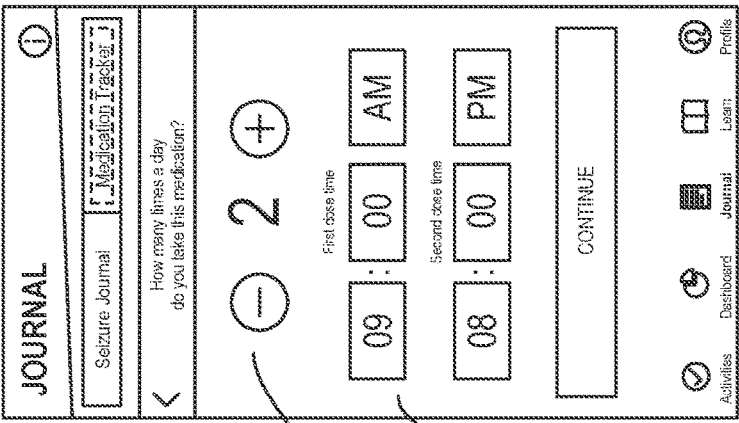
FIG. 8A illustrates an exemplary screen shot of a dosage input for a journal feature according to an embodiment of the computer application of the present invention.

FIG. 8A illustrates an exemplary screen shot of a dosage input for a journal feature according to an embodiment of the computer application of the present invention. FIG. 8B illustrates an exemplary screen shot of a label color selection for the new medication for a journal feature according to an embodiment of the computer application of the present invention. The medication tracker also includes a feature for adding a dosage for the medication and labeling the medication with a color, for easy identification throughout the computer application.

Figure 9:
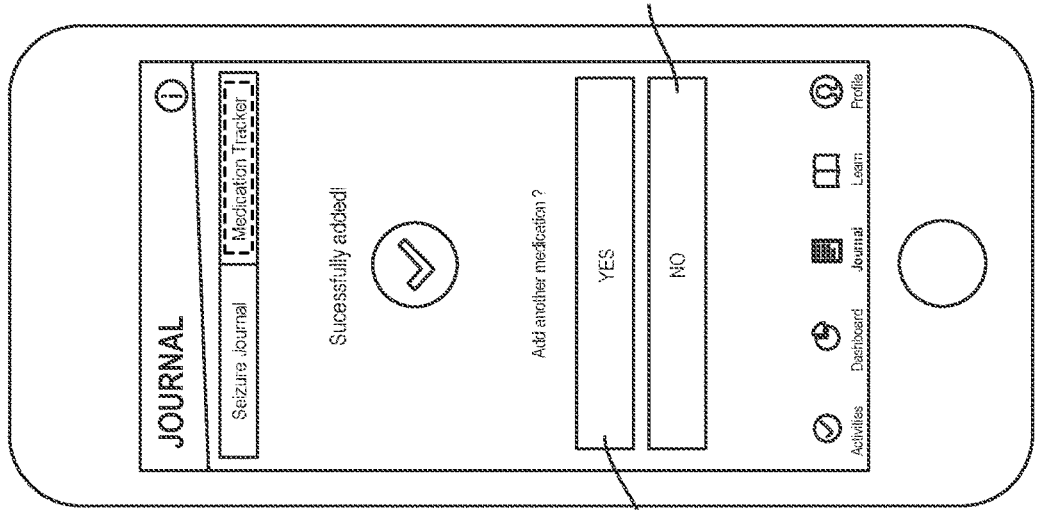
FIG. 9 illustrates an exemplary screen shot of a successfully added medication for a journal feature according to an embodiment of the computer application of the present invention.

FIG. 9A illustrates an exemplary screen shot of a main view of the medication tracker feature with added medications for a journal feature according to an embodiment of the computer application of the present invention, and FIG. 9B illustrates an exemplary screen shot of dosages for a journal feature according to an embodiment of the computer application of the present invention. This feature allows for dosages to be tracked. This feature also allows the user to view all dosages to confirm that medication is being taken according to instructions.

Figure 10B:
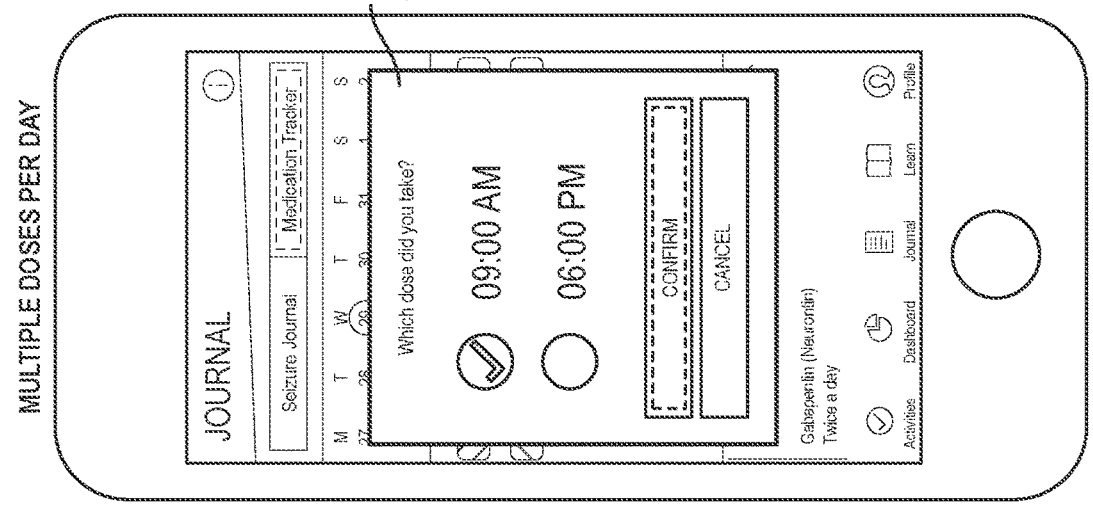
FIG. 10B illustrates an exemplary screen shot of dosages for a journal feature according to an embodiment of the computer application of the present invention.
Figure 10A:
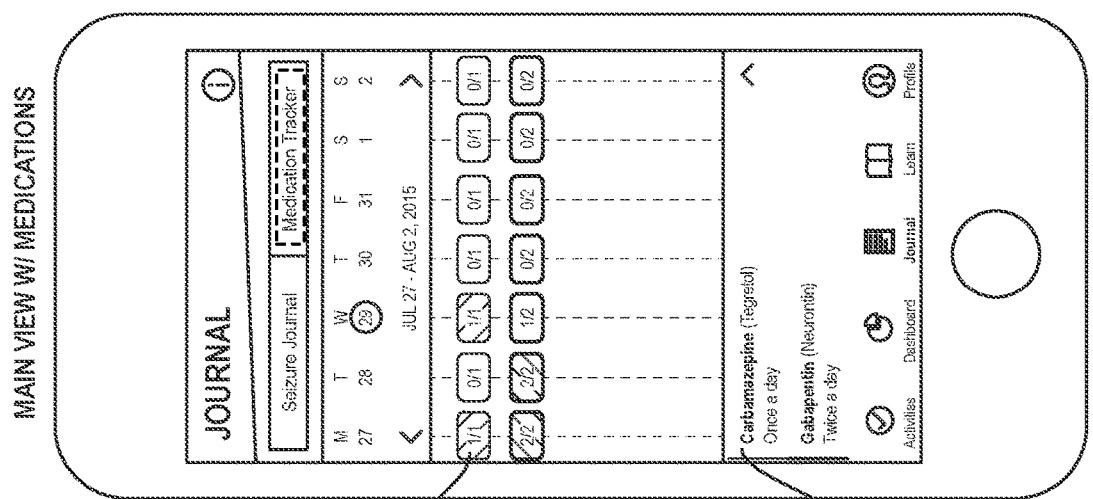
FIG. 10A illustrates an exemplary screen shot of a main view of the medication tracker feature with added medications for a journal feature according to an embodiment of the computer application of the present invention.

FIG. 10A an exemplary screen shot of medication tracking functionality for a journal feature according to an embodiment of the computer application of the present invention; FIG. 10B illustrates an exemplary screen shot of editing a medication for a journal feature according to an embodiment of the computer application of the present invention; and FIG. 10C illustrates an exemplary screen shot of deleting a medication for a journal feature according to an embodiment of the computer application of the present invention. Medications and dosages can also be edited, as illustrated in FIGS. 10A-10C.

FIG. 11 illustrates an exemplary screen shot of a successfully added medication for a journal feature according to an embodiment of the computer application of the present invention. After a medication has been successfully added the user is given the opportunity to return to the home screen or add another medication.

Figure 12:
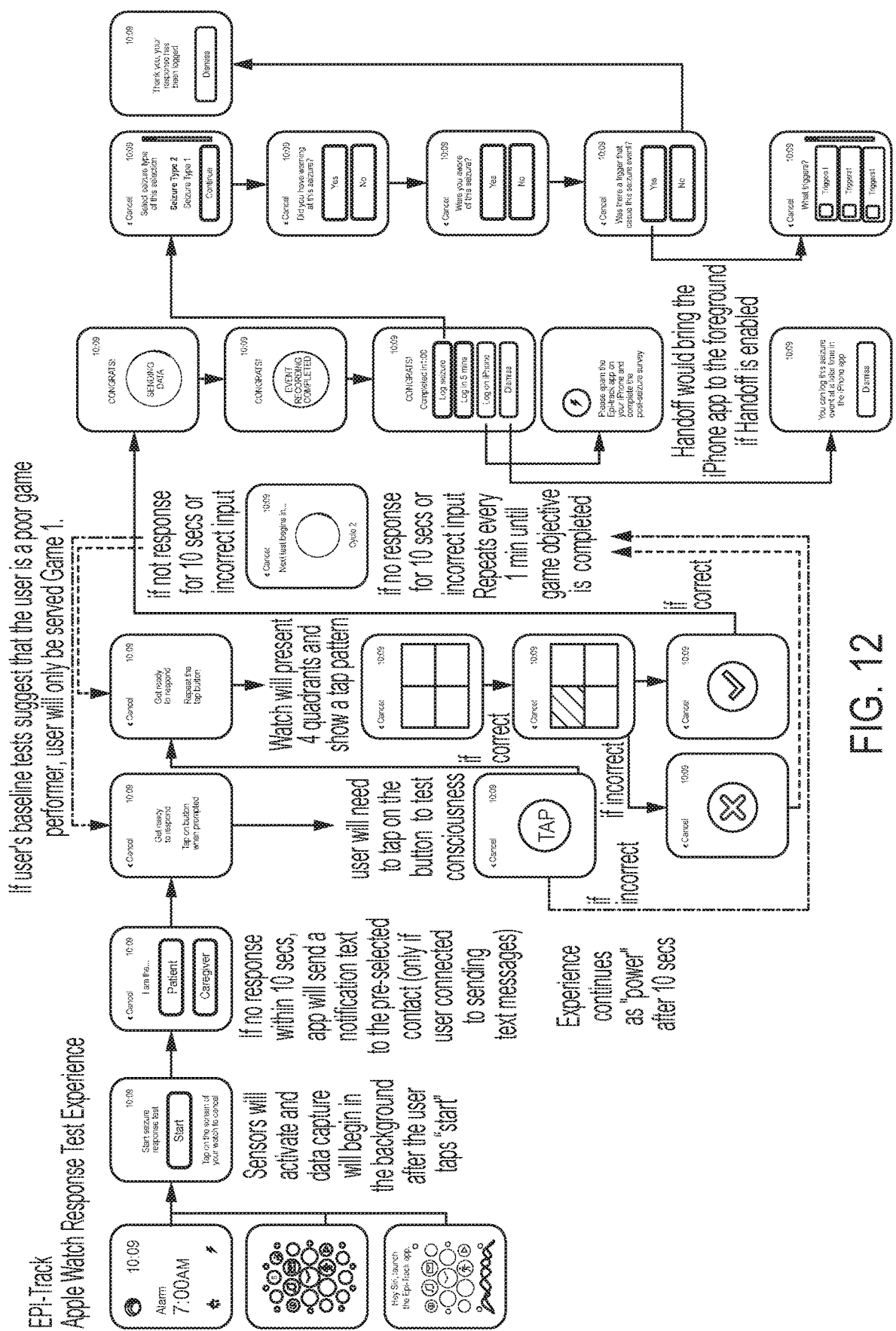
FIG. 12 illustrates a flow diagram of an exemplary user experience for using the computer application according to an embodiment of the present invention.

FIG. 12 illustrates a flow diagram of an exemplary user experience for using the computer application according to an embodiment of the present invention. The flow chart includes exemplary screen shots from a smart wearable for logging a seizure with the computer application.

Figure 13:
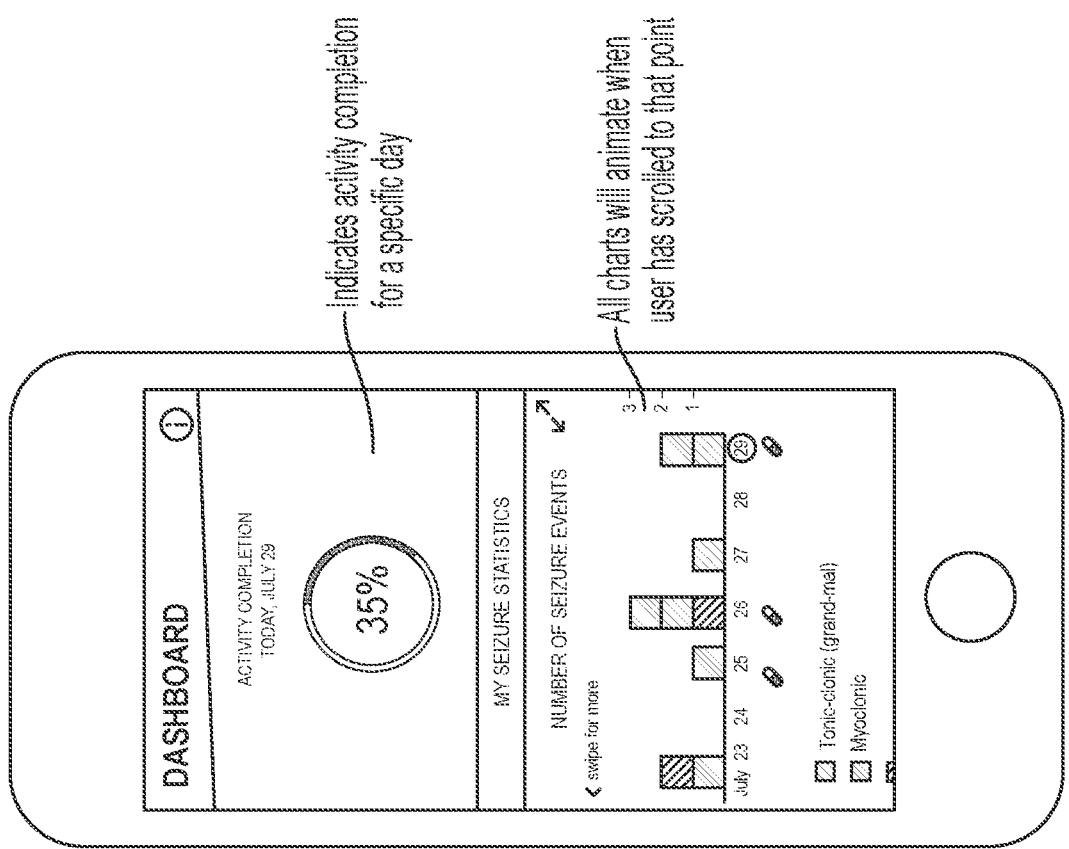
FIG. 13 illustrates an exemplary screen shot for a dashboard feature according to an embodiment of the computer application of the present invention.
Figure 14:
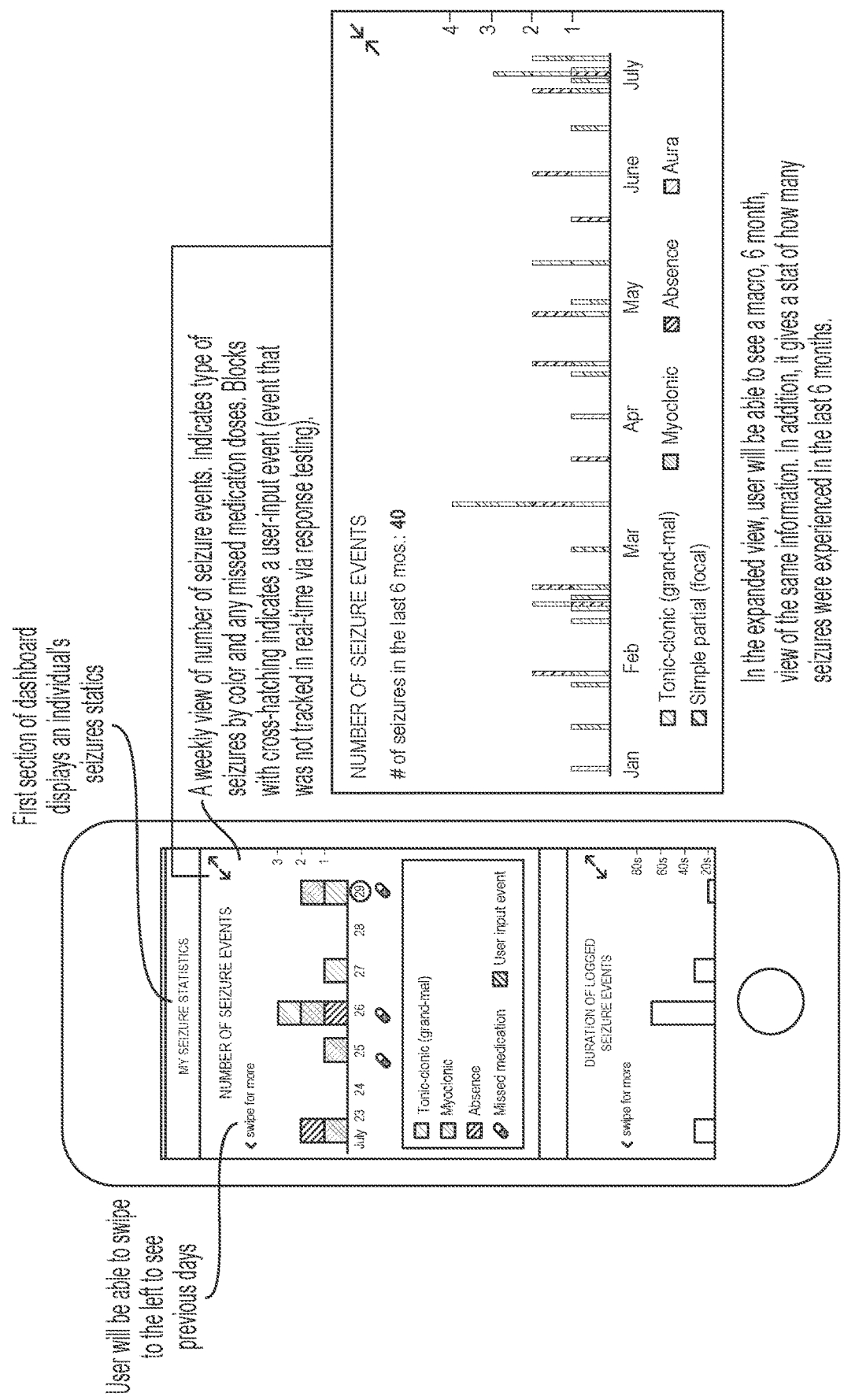
FIGS. 14-18 illustrates an exemplary screen shot and schematic diagram for a user's seizure statistics according to an embodiment of the computer application of the present invention.
Figure 15:
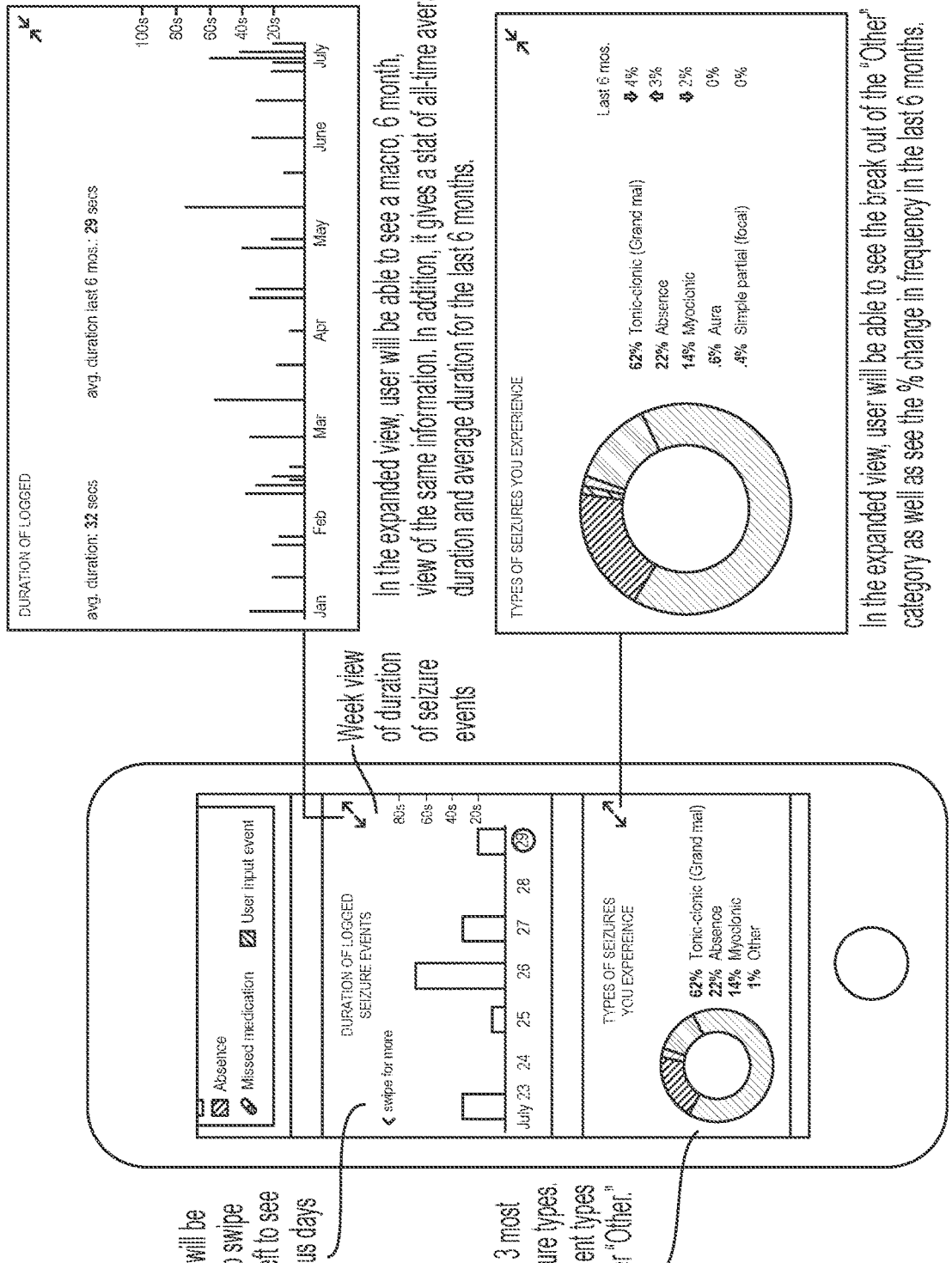
Figure 16:
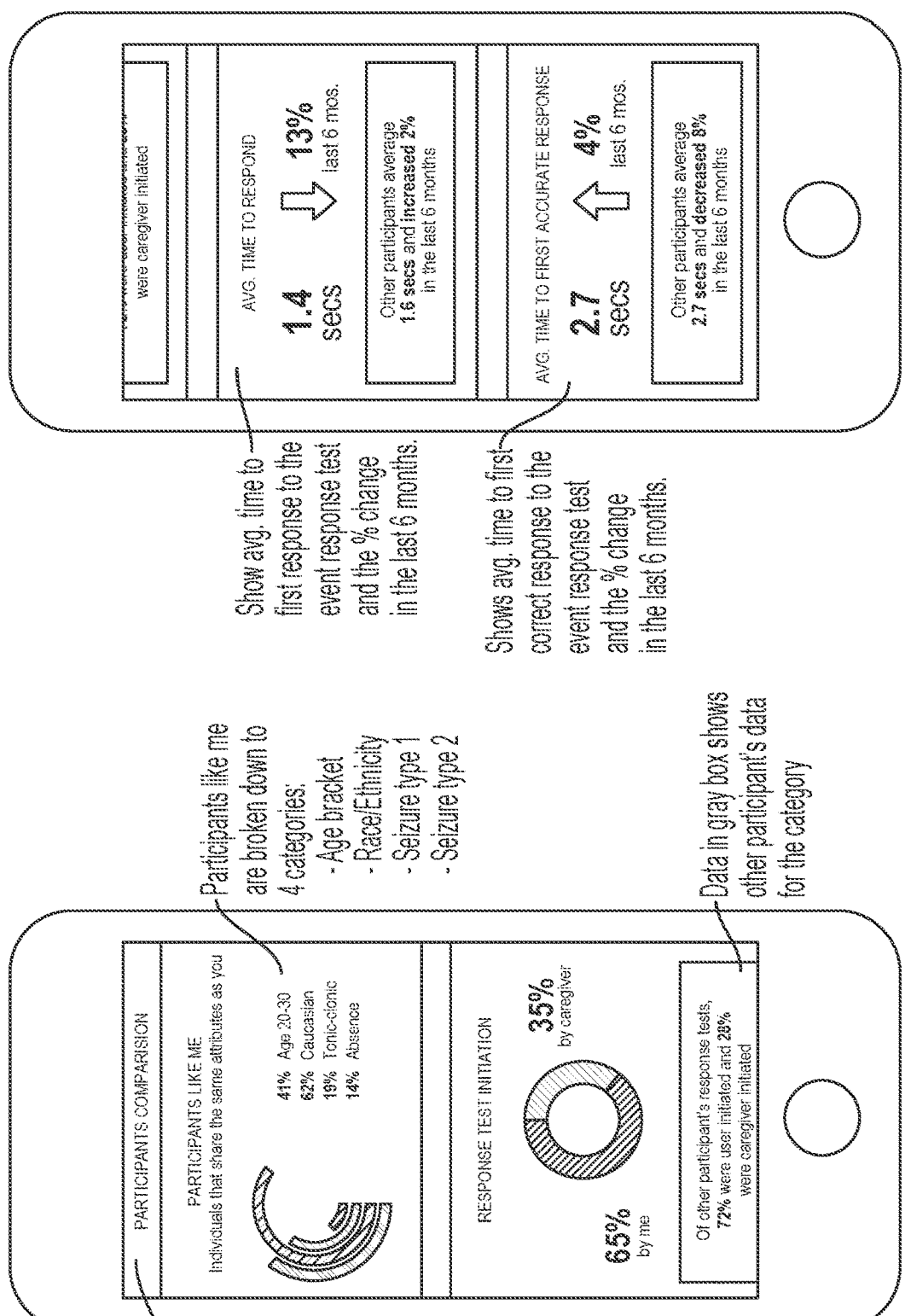
Figure 17:
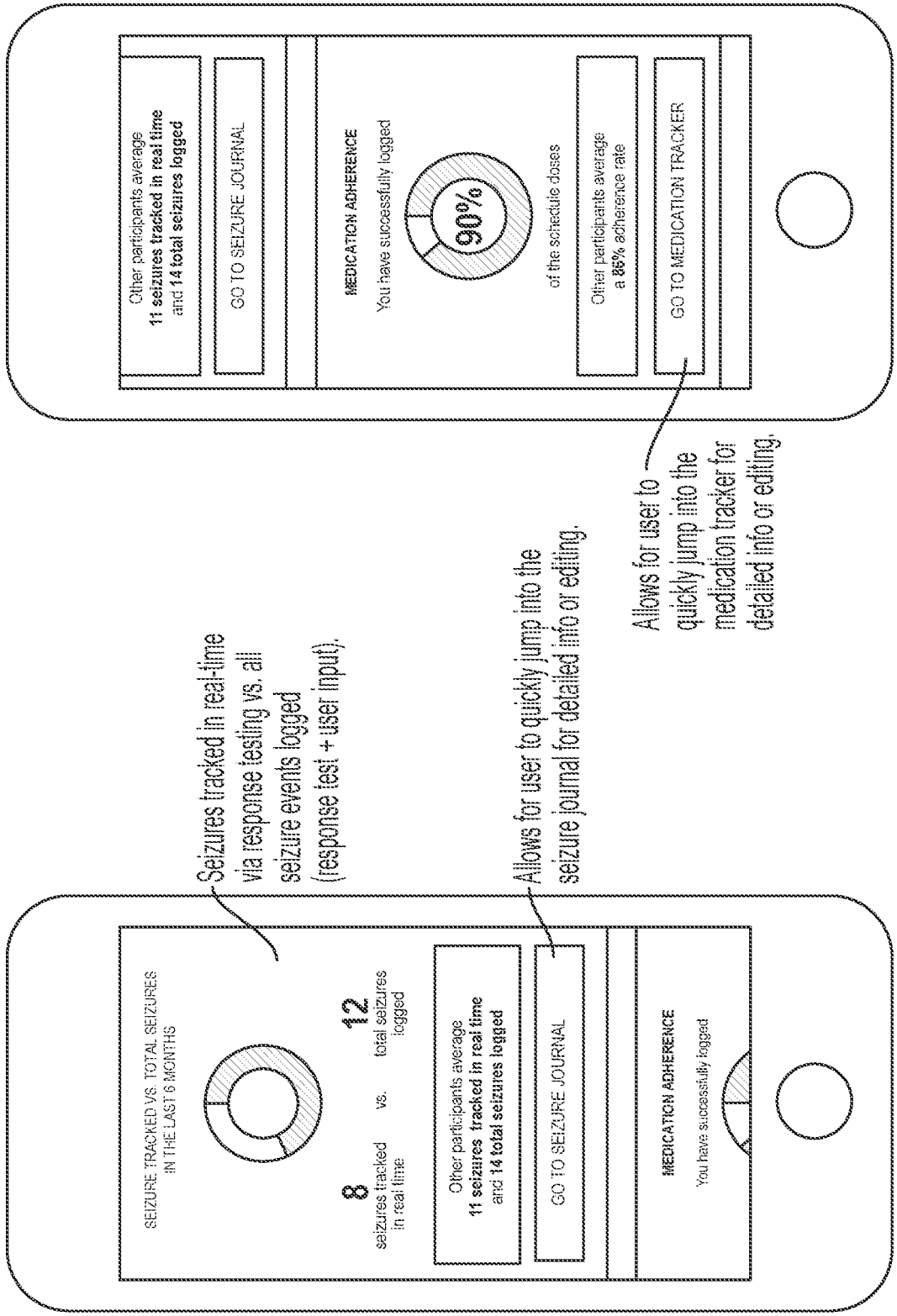
Figure 18:
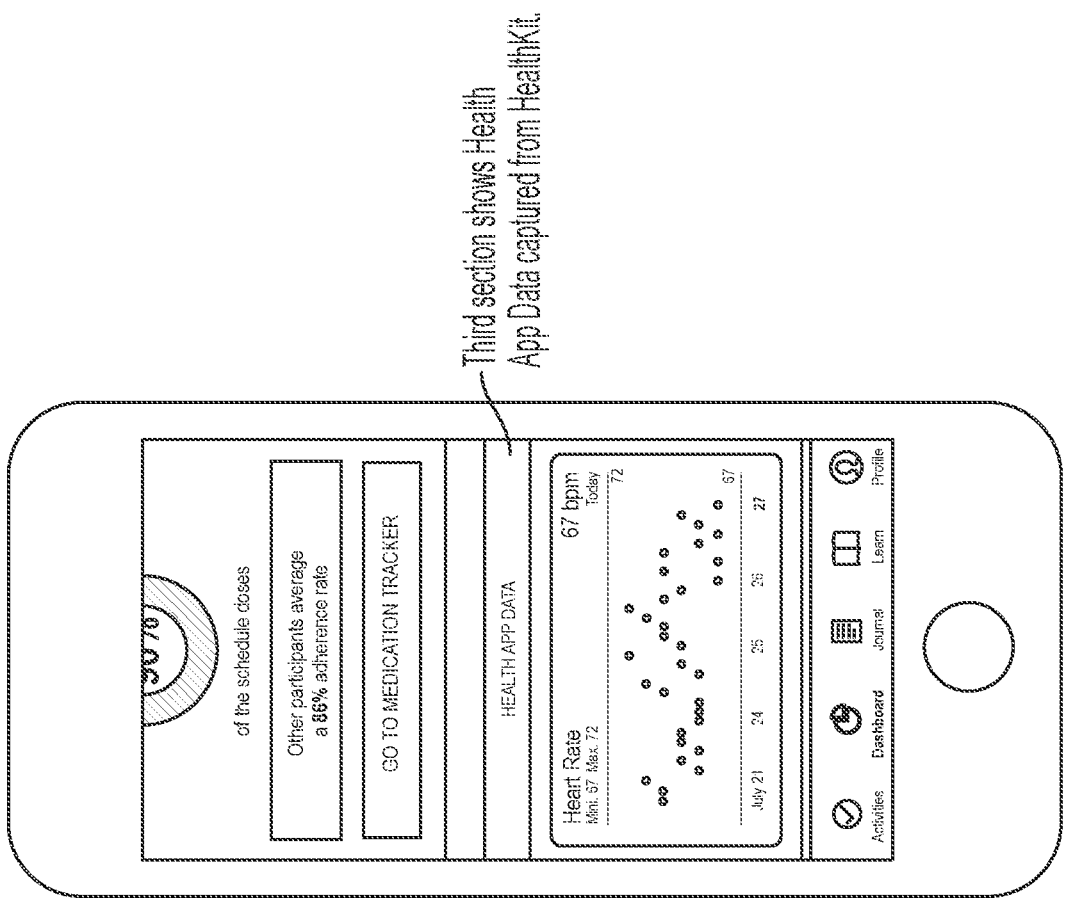

FIG. 13 illustrates an exemplary screen shot for a dashboard feature according to an embodiment of the computer application of the present invention, and FIGS. 14-18 illustrates an exemplary screen shot and schematic diagram for a user's seizure statistics according to an embodiment of the computer application of the present invention. These figures show that the user is provided with graphical representations of the user's seizures and also comparison of the user to other users of the computer application.

The computer application can also be configured to communicate with a contact such as a caregiver, physician, or emergency medical contact. In such an embodiment, if the user has been experiencing a seizure that extends beyond 10 minutes, one of these contacts can be alerted in order to secure potentially life-saving assistance for the user of the computer application. The alert can be configured to appear on the contact's phone or computer. This can be done with a corresponding application on the contact's telephone. Alternately, an alert can pop up on the contact's phone using an emergency alert function of the device.

It should be noted that the computer application is programmed onto a non-transitory computer readable medium that can be read and executed by any of the computing devices mentioned in this application, such as smart watches, smart wearables, smart phones, tablets, phablets, laptop computers, personal computers, servers etc. The non-transitory computer readable medium can take any suitable form known to one of skill in the art. The non-transitory computer readable medium is understood to be any article of manufacture readable by a computer. Such non-transitory computer readable media includes, but is not limited to, magnetic media, such as floppy disk, flexible disk, hard, disk, reel-to-reel tape, cartridge tape, cassette tapes or cards, optical media such as CD-ROM, DVD, blu-ray, writable compact discs, magneto-optical media in disc, tape, or card form, and paper media such as punch cards or paper tape. Alternately, the program for executing the method and algorithms of the present invention can reside on a remote server or other networked device. Any databases associated with the present invention can be housed on a central computing device, server(s), in cloud storage, or any other suitable means known to or conceivable by one of skill in the art. All of the information associated with the application is transmitted either wired or wirelessly over a network, via the internet, cellular telephone network, or any other suitable data transmission means known to or conceivable by one of skill in the art.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

What is claimed is:

1. A method of tracking seizures in a user, comprising:

gathering, by a device, real-time data associated with the user, the device being a smart watch, the device including an interactive user interface to identify and confirm seizures, the interactive user interface for communication between the user and the device, and the interactive user interface including at least a touchscreen for the user to input real-time responses to responsiveness testing, the real-time responses to the responsiveness testing to be input into a seizure tracking application associated with the device based on information corresponding to the real-time responses input by the user via the touchscreen, the information to be used to classify occurrence, type, severity, and duration of the seizure, the device including one or more of:

one or more sensors to gather heart rate data, one or more sensors to measure movement, or one or more sensors for physiological measurements;

providing, by the device and via the interactive user interface of the device, a seizure tracking function of the seizure tracking application, the seizure tracking function of the seizure tracking application to be activated by the user or upon detecting an occurrence of a seizure;

administering, by the device, a first test associated with the responsiveness testing to determine whether there is seizure-related loss of consciousness, the first test including prompting the user to tap on a target on the interactive user interface within a predetermined time, and the first test being repeated at regular intervals until the user is able to complete the first test;

administering, by the device and based on the user completing the first test, a second test associated with the responsiveness testing, to assess whether the user is experiencing seizure-related impairment of awareness based on inability to complete a memory test on the smart watch, the second test including prompting the user by providing for display a tap pattern and requiring the user to repeat the tap pattern, the first test and second test being repeated based on one or more of:

incorrect input, or unresponsiveness, and the second test being repeated at regular intervals until the user is able to complete the second test, to determine a duration of the seizure-related impairment of awareness;

gathering, by the device, the real-time responses to the responsiveness testing for detecting seizure-related loss of consciousness and/or seizure-related impairment of awareness, the real-time responses to the responsiveness testing being used to detect the occurrence, type, severity, and duration of the seizure;

determining, by the device and based on the real-time data and the responsiveness testing, information associated with the occurrence, type, severity, and duration of the seizure;

providing, by the device, one or more post-seizure questions to be answered by the user post-seizure;

receiving, by the device, one or more answers to the one or more post-seizure questions to confirm and validate the occurrence, type, severity, and duration of the seizure;

transmitting, by the device, the real-time data, the real-time responses, the one or more answers to the one or more post-seizure questions, and information associated with the occurrence, type, severity, and duration of the seizure; and receiving, by the device, information related to modification of one or more of lifestyle, medical adherence, or other habits that could affect a risk of subsequent seizures.

2. The method of claim 1, further comprising:

transmitting an alert to a contact depending on the duration and the severity of the seizure associated with the user.

3. The method of claim 1, further comprising:

providing a journal feature to the user for recording information related to the seizure including triggers and medications.

4. The method of claim 1, further comprising:

transmitting an alert if the user has been experiencing the seizure for a time period greater than a predetermined period of time.

5. The method of claim 1, further comprising:

providing a daily prompt to the user of the smart watch to input information associated with occurrence of the seizure or missed medication.

6. The method of claim 1, further comprising:

determining a trigger factor based upon information gathered via the smart watch.

7. The method of claim 1, further comprising:

collecting baseline data associated with the user upon initiation of the application associated with the smart watch, the baseline data including data associated with responses to the memory test.

8. The method of claim 1, wherein the responsiveness testing includes tapping on the target on the touchscreen according to the tap pattern.

9. A smart watch, comprising:

one or more sensors to record user movement data and heart rate data associated with a user of the smart watch for a predetermined period of time;

an interactive user interface to identify and confirm seizures, the interactive user interface for communication between the user and the smart watch, and the interactive user interface including at least a touchscreen for the user to input real-time responses to responsiveness testing, the real-time responses to the responsiveness testing to be input into a seizure tracking application associated with the smart watch based on information corresponding to the real-time responses input by the user via the touchscreen,
the information to be used to classify occurrence, type, severity, and duration of the seizure;
one or more memories; and
one or more processors, communicatively coupled to the one or more memories, configured to:
provide, via the interactive user interface of the smart watch, a seizure tracking function of the seizure tracking application,
the seizure tracking function to be activated by the user or upon detecting an occurrence of a seizure;
prompt, via the interactive user interface, the user of the smart watch to confirm the user of the smart watch wants to track the seizure associated with the user;
administer a first test associated with the responsiveness testing to determine whether there is seizure-related loss of consciousness,
the first test including prompting the user to tap on a target on the interactive user interface within a predetermined time, and
the first test being repeated at regular intervals until the user is able to complete the first test;
administer, based on the user completing the first test, a second test associated with the responsiveness testing, to assess whether the user is experiencing seizure-related impairment of awareness based on inability to complete a memory test on the smart watch,
the second test including prompting the user by providing for display a tap pattern and requiring the user to repeat the tap pattern,
the first test and second test being repeated based on one or more of:
incorrect input, or
unresponsiveness, and
the second test being repeated at regular intervals until the user is able to complete the second test, to determine a duration of the seizure-related impairment of awareness;
record the real-time responses to the responsiveness testing for detecting seizure-related loss of consciousness and/or seizure-related impairment of awareness,
the real-time responses to the responsiveness testing being used to detect the occurrence, type, severity, and duration of the seizure;
determine, based on the real-time responses to the responsiveness testing, information associated with the occurrence, type, severity, and duration of the seizure;
prompt, via the interactive user interface, the user of the smart watch to complete one or more post-seizure questions to be answered by the user post-seizure;
receive one or more answers to the one or more post-seizure questions to confirm and validate the occurrence, type, severity, and duration of the seizure;
record, via the interactive user interface, the one or more answers to the one or more the post-seizure questions;
transmit the user movement data, the heart rate data responsiveness, the one or more answers to the one or more post-seizure questions, and information associated with the occurrence, type, severity, and duration of the seizure; and receive information related to modification of one or more of lifestyle, medical adherence, or other habits that could affect a risk of subsequent seizures.

10. The smart watch of claim 9, where the one or more processors are further configured to:
transmit an alert to a predetermined contact depending on the duration and the severity of the seizure associated with the user.

11. The smart watch of claim 9, where the one or more processors are further configured to:
provide a journal feature to the user of the smart watch for recording information related to the seizure associated with the user including triggers and medications.

12. The smart watch of claim 9, where the one or more processors are further configured to:
transmit an alert if the user has been experiencing the seizure for a time period greater than the predetermined period of time.

13. The smart watch of claim 9, where the one or more processors are further configured to:
transmit an alert to a predetermined care giver if the user is non-responsive to prompts.

14. The smart watch of claim 9, where the one or more processors are further configured to:
record metrics associated with one or more sensor devices of the smart watch during the seizure for the predetermined period of time; and
provide a notification to a predetermined contact if the seizure continues beyond the predetermined period of time.

15. The smart watch of claim 9, where the one or more processors are further configured to:
collect baseline data associated with the user upon initiation of the application associated with the smart watch,
the baseline data including data associated with responses to the memory test, and
the data associated with the responses to the memory test corresponding to a previous response to the memory test.

16. A non-transitory computer readable medium storing instructions, the instructions comprising:
one or more instructions that, when executed by one or more processors, cause the one or more processors to:
provide, via an interactive user interface of a smart watch, a seizure tracking function of an application associated with the smart watch,
the interactive user interface including at least a touchscreen for a user to input real-time responses to responsiveness testing,
the real-time responses to the responsiveness testing to be input into the application associated with the smart watch based on information corresponding to the real-time responses input by the user via the touchscreen,
the information to be used to classify occurrence, type, severity, and duration of the seizure,
the seizure tracking function to be activated by the user or upon detecting an occurrence of a seizure;
prompt the user, via the interactive user interface of the smart watch, to confirm the user wants to track the seizure;
administer a first test associated with the responsiveness testing to determine whether there is seizure-related loss of consciousness,
the first test including prompting the user to tap on a target on the interactive user interface within a predetermined time, and the first test being repeated at regular intervals until the user is able to complete the first test;

administer, based on the user completing the first test, a second test associated with the responsiveness testing, to assess whether the user is experiencing seizure-related impairment of awareness based on inability to complete a memory test on the smart watch, the second test including prompting the user by providing for display a tap pattern and requiring the user to repeat the tap pattern, the first test and second test being repeated based on one or more of:
incorrect input, or
unresponsiveness, and the second test being repeated at regular intervals until the user is able to complete the second test, to determine a duration of the seizure-related impairment of awareness;

record real-time responses to the first test and the second test, the real-time responses to the responsiveness testing being used to detect the occurrence, type, severity, and duration of the seizure;

determine, based on the real-time responses to the responsiveness testing, information associated with the occurrence, type, severity, and duration of the seizure;

prompt the user to answer, post-seizure, one or more post-seizure questions;

record one or more answers to the one or more post-seizure questions to confirm and validate the occurrence, type, severity, and duration of the seizure;

transmit user movement data, heart rate data, responsiveness, the one or more answers to the one or more post-seizure questions, and information associated with the occurrence, type, severity, and duration of the seizure; and receive information for modification of one or more of lifestyle, medical adherence, or other habits that could affect a risk of subsequent seizures.

17. The non-transitory computer readable medium of claim 16, where the one or more instructions, when executed by the one or more processors, further cause the one or more processors to:
transmit an alert to a predetermined contact based on the duration and the severity of the seizure associated with the user.

18. The non-transitory computer readable medium of claim 16, where the one or more instructions, when executed by the one or more processors, further cause the one or more processors to:
transmit an alert if the user has been experiencing the seizure for a time period greater than a predetermined period of time.

19. The non-transitory computer readable medium of claim 16, where the one or more instructions, when executed by the one or more processors, further cause the one or more processors to:
transmit an alert to a predetermined care giver if the user is non-responsive to prompts.

20. The non-transitory computer readable medium of claim 16, where the one or more instructions, when executed by the one or more processors, further cause the one or more processors to:
collect baseline data associated with the user upon initiation of the application associated with the smart watch,
the baseline data including data associated with responses to the memory test, and
the data associated with the responses to the memory test corresponding to a previous response to the memory test.

21. The non-transitory computer readable medium of claim 16, where the one or more instructions, when executed by the one or more processors, further cause the one or more processors to:
record metrics associated with one or more sensor devices of the smart watch during the seizure for a predetermined period of time; and
provide a notification to a predetermined contact if the seizure continues beyond the predetermined period of time.

* * * * *